United States Patent [19]

Isaksson et al.

[11] Patent Number: 5,817,765
[45] Date of Patent: Oct. 6, 1998

[54] PURIFICATION OF PLASMA PROTEINS

[75] Inventors: Sven Isaksson, Vårby; Stefan Winge, Stockholm, both of Sweden

[73] Assignee: Pharmacia & Upjohn Aktiebolag, Stockholm, Sweden

[21] Appl. No.: 537,872

[22] PCT Filed: May 6, 1994

[86] PCT No.: PCT/SE94/00422

§ 371 Date: Oct. 30, 1995

§ 102(e) Date: Oct. 30, 1995

[87] PCT Pub. No.: WO94/26287

PCT Pub. Date: Nov. 24, 1994

[30] Foreign Application Priority Data

May 7, 1993 [SE] Sweden ................. 9301582

[51] Int. Cl.$^6$ .................. C07K 1/00; A61K 35/14
[52] U.S. Cl. .................. 530/364; 530/380; 530/392; 530/393; 530/394; 530/414; 530/418; 530/419; 530/422; 530/427
[58] Field of Search .................. 530/364, 380, 530/392, 393, 394, 414, 418, 419, 422, 427

[56] References Cited

U.S. PATENT DOCUMENTS

| | | | |
|---|---|---|---|
| 4,684,723 | 8/1987 | Dove et al. | 530/351 |
| 4,764,369 | 8/1988 | Neurath et al. | 424/89 |
| 4,789,545 | 12/1988 | Woods et al. | 424/101 |
| 4,820,805 | 4/1989 | Neurath et al. | 530/410 |
| 5,395,923 | 3/1995 | Bui-Khac et al. | 530/381 |

FOREIGN PATENT DOCUMENTS

| | | |
|---|---|---|
| 0 131 740 A2 | 1/1985 | European Pat. Off. |
| 0 218 090 A2 | 4/1987 | European Pat. Off. |
| 0 239 859 A3 | 10/1987 | European Pat. Off. |
| WO 90/05140 | 5/1990 | WIPO |

OTHER PUBLICATIONS

Ramelmeier et al., The partitioning of cholesterol oxidase in Triton X–114–based aqueous two–phase systems, Bioseparation, vol. 2 (1991), pp. 315–324.

Liu et al, *I.N.S.E.R.M.*, vol. 175, pp.–263–1989.

Piet et al, *Transfusion.*, vol. 30, No. 7, pp. 591–598, 1990.

Hellsternal et al. *Vox Sanguinis*, vol. 63, No. 3, pp. 178–185, 1992.

Raunelureier et al, *Bioseparation*, vol. 2, pp. 315–324, 1991.

Glasstone, Textbook of Physical Chemistry Second Edition–Fourth Printing, D. Van Nostrand Company, Inc. 99. 1254–1259.

*Primary Examiner*—Cecilia J. Tsang
*Assistant Examiner*—Abdel A. Mohamed
*Attorney, Agent, or Firm*—Pollock, Vande Sande & Priddy

[57] ABSTRACT

Virus inactivating chemicals and/or detergents in an aqueous composition containing a water-soluble plasma protein are reduced by selecting a suitable combination of temperature and concentration above 0.5M of salt with a high salting out effect according to the Hofmeister series, thereby forming vesicles containing the virus inactivating chemical and/or detergent. These vesicles are removed from the aqueous phase, e.g. by phase separation or filtration, and the protein thereafter isolated from the aqueous phase. The water-soluble plasma protein can be e.g. antithrombin III, transferrin or albumin. When the aqueous phase comprises e.g. a salt of citrate or sulphate in a concentration above 1M at room temperature, the reduction of virus inactivating chemical or detergent can be as high as 2000 times or more, giving a final concentration below 5 ppm.

23 Claims, No Drawings

PURIFICATION OF PLASMA PROTEINS

This invention relates to a process for reduction of virus inactivating chemicals and/or detergents in an aqueous composition containing a water-soluble plasma protein. By selecting a suitable combination of temperature and concentration above 0.5M of a salt with a high salting out effect according to the Hofmeister series, vesicles containing the virus inactivating chemical and/or detergent are formed. These vesicles are removed from the aqueous phase, e.g. by phase separation or filtration, and the protein thereafter isolated from the aqueous phase. When the aqueous phase comprises a salt of citrate or sulphate in a concentration above 1M at room temperature, the reduction of virus inactivating chemical or detergent can be as high as 2000 times or more, giving a final concentration below 5 ppm.

BACKGROUND OF THE INVENTION

The inactivation of virus in blood products such as factor VIII, albumin, factor IX and antithrombin is a known problem for manufacturers. This has normally been solved by heating. If the product is not inactivated by such a process, adding of virus inactivating chemicals may be used. In this case, however, there is a need for removing the added chemicals before use of the medical products.

EP-A-0 218 090 (Miles Laboratories) relates to a process for separating and recovering proteins or nucleic acids, from an aqueous system also containing a component having the ability to create two liquid phases by use of salt partitioning technology. In this process, a polymer and a water soluble salt, such as potassium or sodium phosphate or ammonium sulphate, are added to the protein or nucleic acid, whereupon the resulting solution is left to separate. Information about virus inactivating chemicals or detergents is lacking, as is information about techniques to reduce the concentration of such compounds to a pharmaceutically acceptable level.

EP-A-0 239 859 (New York Blood Center) relates to a method for removing lipid soluble process chemicals, such as virus inactivating solvents and/or detergents, from biological materials, by contacting the biological material with an oil extract, agitating the resultant mixture, separating out an upper phase and a lower phase by sedimentation or centrifugation, and decanting the upper phase containing oil and extracted process chemicals. There is no information about addition of organic or inorganic salts with a high salting out effect or the possible advantage derived by their presence. The lack of these salts in the aqueous phase necessitates a complicated process with repeated extraction steps to arrive at a sufficiently low level of the virus inactivating solvents and/or detergents.

Another method is disclosed in EP-A-0 131 740 (New York Blood Center), in which a protein-containing composition is virus inactivated by contacting the composition with di- or trialkylphosphate, preferably in the presence of a non-ionic detergent. According to this disclosure, the di- or trialkylphosphate is removed by precipitation of the protein with glycine and sodium chloride. The detergent can be removed by several steps, chosen among diafiltration, adsorption on chromatographic supports and precipitation.

These methods may be laborious, time consuming and may often not give a satisfying reduction of detergents and virus inactivating chemicals.

From an article by R. A. Ramelmeier et al, Bioseparation 2; 315–324, 1991, it is known that a hydrophobic enzyme can be purified from fermentation broths in a detergent based aqueous two-phase system by variation of e.g. temperature and salt concentration. No higher salt concentration than 0.2M was used. The enzyme is recovered in the detergent phase and can be recovered to 80–90%.

DESCRIPTION OF THE INVENTION

We have now surprisingly found that when the concentration of certain salts is increased to above 0.5M in a composition containing a plasma protein (either fractionated from plasma or recombinant produced), a virus inactivating chemical, preferably tri-n-butyl phosphate (TNBP), and/or a detergent, preferably a TRITON®, the concentration of TNBP can be reduced to below 1 ppm and the concentration of TRITON can be reduced to below 5 ppm in the aqueous phase.

We have thus found a process for purifying a protein composition to which virus inactivating chemicals or detergents or mixtures thereof, have been added. This one-step process is easier to perform than the earlier known multi-step processes. Furthermore, the present process can be carried out rapidly, since the formation of vesicles will be close to instantaneous. Also, the process gives a lower or equal amount of the virus inactivating chemicals and detergents in the final product than the earlier known processes.

The invention thus relates to a process for reducing the concentration of virus inactivating chemicals and/or detergents in an aqueous composition containing a water-soluble plasma protein, characterized by forming vesicles containing the virus inactivating chemical and/or detergent by selecting a suitable combination of temperature and concentration above 0.5M of a salt with a high salting out effect according to the Hofmeister series, and thereafter removing essentially all the vesicles from the aqueous phase, and subsequently isolating the protein from the aqueous phase.

The present invention can be carried out at a temperature of the composition in the range of from 0° C. up to 70° C. Below 0° C., the composition is frozen or the viscosity is at least high. Above 70° C., the proteins are likely to be denaturated more or less completely thereby losing their activity. The temperature of the composition is suitably in the range of from 10° C. up to 50° C., and preferably from 20° C. up to 30° C., Generally, the addition of large amounts of electrolytes to lyophilic sols, i.e. compositions containing very small hydrophilic particle results in the dispersed substance being precipitated. The effect is called "salting out". The salting-out effect depends on the nature of the ions, mainly the anion but also the cation involved. The ions can be arranged in order of their ability to remove lyophilic substances from colloidal solutions. This is sometimes called the Hofmeister series or, more generally, the lyotropic series. Reference is here made to S. Glasstone, *Textbook of Physical Chemistry*, van Nostrand Co., Toronto, 2nd ed., Apr. 1946, p. 1254–1259. Salts with a high salting out effect according to the Hofmeister series are those with an anion with a higher salting out effect than the chloride ion. Anions in this region include mono-, di- and trivalent anions. Di- or trivalent anions are suitably used in the present invention, preferably trivalent anions. The major examples of the anions in this region are citrate, tartrate, sulphate, acetate, phosphate and fluoride, with citrate, tartrate and sulphate being preferred. Cations that can be used to advantage in the present invention are monovalent cations, such as lithium, sodium, ammonium and potassium. For reasons of simplicity and pharmaceutically acceptable additives, sodium, ammonium or potassium are preferred, sodium being most preferable. Thus, especially preferred salts in the present invention are sodium citrate, sodium tartrate and sodium sulphate. It is also within the scope of the present invention, that mixtures of salts with different anions and/or cations as disclosed above, can be used to advantage. Also, addition of the same or different salts as disclosed above, can be carried out to advantage in a sequence.

The inventors of the present invention have now surprisingly found that when the salt concentration is increased above 0.5M according to the present invention, the virus inactivating chemical and/or detergent will form vesicles, preferably micelles, in the solution instead of being precipitated. The formation of vesicles and the reduction in concentration of virus inactivating chemicals and/or detergents obtainable thereby, is dependent upon the combination of temperature and concentration of the salt with a high salting out effect in the aqueous phase. At room temperature the salt concentration is preferably above 1M. By increasing the temperature above room temperature a lower salt concentration can be used. At lower temperatures a higher salt concentration is necessary. The temperature can be between 0° C. and 70° C. and the salt concentration should then be above 1.5 and 0.5M, respectively. The concentration of the salt should not exceed 2.5M, since this will bring about precipitation of the salt and/or protein. Preferably, the salt concentration is below 2.0M.

The vesicles can be removed from the aqueous phase, e.g. by phase separation, filtration or centrifugation or sequences thereof, preferably a sequence of phase separation followed by filtration. When the vesicles are removed by phase separation, the composition is left for a residence time such that the virus inactivating chemical and/or detergent are essentially completely recovered at the upper surface of the aqueous phase or, if oil is present, in or at the upper surface of the oil phase. Thus, an oil, e.g. soybean oil, is preferably added to the composition before the phase separation. In this way, the vesicles are separated quicker and more completely from the protein-containing aqueous phase. A suitable residence time with oil present lies in the range of from about 10 min up to about 2 hours. A suitable residence time without oil being present, lies in the range of from about 15 mins. up to about 4 hours. When filtration is used to remove the vesicles this can be carried out almost immediately, since the vesicles are formed instantaneously under the carefully selected conditions of the present invention.

The virus inactivating chemicals used are generally hydrophobic in nature, as is at least a part of the detergent molecules. The virus inactivating chemicals used can be dialkyl- or trialkylphosphates having branched or unbranched, substituted or unsubstituted alkyl gropus, suitably with 1 to 10 carbon atoms. Examples of suitable trialkylphosphatts are those where the alkyl group is n-butyl, t-butyl, n-hexyl, 2-ethylhexyl and n-decyl. The virus inactivating chemical is preferably tri-n-butyl phosphate (TNBP). Mixtures of various dialkylphosphates can also be used, as well as mixtures of various trialkylphosphates. Mixtures of dialkyl-phosphates and trialkylphosphates are also possible to use within the scope of the present invention.

The detergent is suitably a non-ionic detergent, such as a polyoxyethylene ether, e.g. a TRITON®, or a polyoxyethylene sorbitan fatty acid ester, such as polyoxyethylene-(20)-sorbitan monolaurate or polyoxyethylene-(20)-sorbitan monooleate. Preferably, the detergent is TRITON® X-100. For instance, see Merck Index, 11th Edition, item 6681.

The protein can be e.g. factor VIII, factor IX, albumin, transferrin, alpha$_1$-acid glycoprotein or antithrombin III. The protein to be treated can be manufactured according to general methods for fractionating plasma and separating the different plasma proteins, or by recombinant methods.

The virus inactivating step includes the addition of a detergent (e.g. a TWEEN® and/or TRITON® X-100) and a virus inactivating chemical, e.g. tri-n-butyl phosphate (TNBP) to the protein in an aqueous solution. Thereafter, the aqueous solution is stirred. Subsequently, the temperature and salt concentration of the composition are adjusted to form vesicles. To the inactivated solution an oil is preferably added (e.g about 5%). Thereafter, the mixture can be phase separated in a separation device such as separation funnel. The protein can be easily isolated from the aqueous phase, e.g. by diafiltration, desalting, chromatography or precipitation. For a discussion of TWEEN® see Merck Index, 11th Edition, item 7559.

The pH is normally above 5, preferably above 6.

The pharmaceutically acceptable concentration of virus inactivating chemicals and detergents vary depending on the particular compound. With the present process, less than 5 ppm of deterent and less than 1 ppm of the virus inactivating chemical is normally found in the aqueous phase. These concentrations are well below commonly recognized pharmaceutically acceptable concentrations of such compounds. This means that normally no further purification step is needed, other than the isolation of the protein, which is a great advantage in the manufacturing of plasma proteins. However, with albumin a further purification step appears necessary, such as ion exchange or affinity chromatography.

The following Examples are intended to illustrate the invention, without limiting the scope of said invention.

EXAMPLE 1

Antithrombin III (AT III) was manufactured by Pharmacia AB of Sweden, from blood plasma. The AT III had been separated from the plasma by using a Heparin Sepharose gel.

To 100 ml 2% AT III solution, 1.5 g stock solution (3 parts TNBP +10 parts TRITON® X-100) was added. The TNBP and TRITON® X-100 was marketed by Merck of Germany and Union Carbide of the U.S., respectively. The temperature of the solution was adjusted to 24° C. and the solution stirred for at least 3 h. 100 ml buffer containing 2M sodium citrate and 0.05M sodium phosphate was slowly added. The resulting concentration of citrate thus was 1M. The solution was stirred slowly during the addition. Soybean oil was then added to about 5%. The solution was slowly stirred for 30 minutes and then left to phase separate for 90 minutes.

Micelles were found in or at the upper surface of the oil phase. In the aqueous bottom phase where AT III was found, the content of TRITON® X-100 was less than 5 ppm and the content of TNBP was less than 1 ppm. The recovery of AT III activity was more than 95%.

EXAMPLE 2

Transferrin, manufactured by Pharmacia AB of Sweden, was isolated from FrIV in "Cohn's cold ethanol method" and further purified by chromatography.

To 100 ml 2% transferrin solution, 1.5 g stock solution (3 parts TNBP +10 parts TRITON® X-100) was added. The temperature of the solution was adjusted to 24° C. and the solution stirred for at least 3 h. 100 ml buffer containing 2M sodium citrate and 0.05M sodium phospate was slowly added. The resulting concentration of citrate thus was 1M. The solution was slowly stirred during the addition and 30 minutes therafter before it was left to phase separate.

The solvent detergent treated solution was split into three equal volumes.

In the first volume the micelles were separated immediately through filtration.

The second volume was left to phase separate without any further treatment. The bottom phase was then analysed for TNBP and TRITON® X-100. Micelles were found in or at the upper surface of the aqueous phase.

Soybean oil was added to the third volume, which subsequently was treated according to Example 1. Micelles were found in or at the upper surface of the oil phase.

With all three methods to separate the micelles from the protein solution, the recovery of transferrin activity in the aqueous phase was more than 95%.

The content of TNBP was less then 1 ppm and the content of TRITON® X-100 was less then 5 ppm with all three methods.

EXAMPLE 3

Antithrombin III (AT III) was manufactured by Pharmacia AB of Sweden, from blood plasma. The AT III had been separated from the plasma by using an Heparin Sepharose gel.

To 100 ml 2% AT III solution, 1.5 g stock solution (3 parts TNBP +10 parts TRITON® X-100) was added. The temperature of the solution was adjusted to 24° C. and the solution stirred for at least 3 h. 100 ml buffer containing 2M sodium sulphate and 0.05M sodium phosphate was slowly added. The resulting concentration of sulphate thus was 1M. The solution was slowly stirred during the addition and for 30 minutes therafter before it was left to phase separate. The solution was then immediately filtrated. In the filtrate more than 95% of the antihrombin III activity was recovered. The content of TRITON® X-100 was less than 5 ppm and the content of TNBP was less than 1 ppm.

EXAMPLE 4

Albumin, manufactured by Pharmacia AB of Sweden, was isolated by a modified "Cohn's cold ethanol method".

To 100 ml 2% albumin solution, 1.5 g stock solution (3 parts TNBP +10 parts TRITON® X-100) was added. The temperature of the solution was adjusted to 24° C. and the solution stirred for at least 3 h. 100 ml buffer containing 2M sodium citrate and 0.02M sodium acetate was slowly added. The resulting concentration of citrate thus was 1M. The solution was slowly stirred during the addition and 30 minutes therafter before it was left to phase separate. The solution was then immediately filtrated.

In the filtrate over 95% of the albumin activity was recovered. The content of TRITON® X-100 was 250 ppm and TNBP 35 ppm.

These higher concentrations of virus inactivating agents in the albumin solution can be explained with the ability of albumin to bind hydrophobic agents. One purpose of albumin is to transport hydrophobic molecules in blood. With albumin, therefore, a further separation is needed, for example a chromatographic step or diafiltration.

We claim:

1. Process for purifying a water-soluble plasma protein in an aqueous composition wherein the protein is selected from the group consisting of antithrombin III, transferrin, factor IX and alpha$_1$-acid glycoprotein by adding a salt to said aqueous composition wherein said aqueous composition further comprises vesicle-forming virus inactivating chemicals or detergents or both, and wherein said process comprises selecting a suitable combination of a temperature in the range of from 0° C. up to 70° C. and a concentration of the salt in the range of from 0.5M to 2.5M, wherein said salt is selected from the group consisting of salts with a high salting out effect according to the Hofmeister series, for forming vesicles containing the virus inactivating chemicals or detergents or both, and thereafter removing essentially all the vesicles from the aqueous phase, and subsequently isolating the protein from the aqueous phase.

2. Process according to claim 1, wherein said salt concentration is above 1M at a temperature in the range from room temperature up to 70° C.

3. Process according to claim 1, wherein said salt concentration is above 1.5M at a temperature in the range from 0° C. up to 70° C.

4. Process according to claim 1, in which the vesicles are removed from the aqueous phase by filtration.

5. Process according to claim 1, in which the water-soluble plasma protein is purified from blood.

6. Process according to claim 1, in which the water-soluble plasma protein is recombinant.

7. Process according to claim 1, in which the concentration of the virus inactivating chemical or detergent or both is reduced to below 5 ppm.

8. Process according to claim 1, wherein the protein is antithrombin III.

9. Process according to claim 1, wherein the protein is transferrin.

10. Process according to claim 1, wherein said salt has an anion selected from the group consisting of citrate, tartrate, sulfate, acetate, phosphate, and mixtures thereof.

11. Process according to claim 10, wherein said salt has an anion selected from the group consisting of citrate, sulfate, and mixtures thereof.

12. Process according to claim 1, wherein the pH is above 5.

13. Process according to claim 12, wherein the pH is above 6.

14. Process according to claim 1, wherein the protein is albumin.

15. Process according to claim 14, in which the protein phase is applied to an ion-exchange or affinity column after the vesicles have been removed from the aqueous phase.

16. Process according to claim 1, in which the virus inactivating chemical is selected from the group consisting of dialkylphosphates, trialkylphosphates, and mixtures thereof.

17. Process according to claim 16, in which the virus inactivating chemical is tri-n-butyl phosphate (TNBP).

18. Process according to claim 1, in which the detergent is a non-ionic detergent.

19. Process according to claim 18, wherein the detergent is a polyoxyethylene ether.

20. Process according to claim 1, in which the vesicles are removed from the aqueous phase by phase separation.

21. Process according to claim 20, wherein an oil is added to the composition before the phase separation.

22. Process according to claim 20, in which the vesicles are removed from the aqueous phase by phase separation followed by filtration.

23. Process for purifying a water-soluble plasma protein in an aqueous composition wherein the protein is selected from the group consisting of antithrombin III and transferring by adding a salt to said aqueous composition wherein said aqueous composition further comprises vesicle-forming virus inactivating chemicals or detergents or both, and wherein said process comprises selecting a suitable combination of a temperature in the range of from 0° C. up to 70° C. and a concentration of the salt in the range of from 0.5M to 2.5 M, wherein said salt is selected from the group consisting of salts with a high salting out effect according to the Hofmeister series, for forming vesicles containing the virus inactivating chemicals or detergents or both, and thereafter removing essentially all the vesicles from the aqueous phase, and subsequently isolating the protein from the aqueous phase.

* * * * *